US006215041B1

(12) United States Patent
Stice et al.

(10) Patent No.: US 6,215,041 B1
(45) Date of Patent: *Apr. 10, 2001

(54) CLONING USING DONOR NUCLEI FROM A NON-QUIESECENT SOMATIC CELLS

(75) Inventors: Steven L. Stice, Belchertown; Jose Cibelli, Amherst; James M. Robl; Paul Golueke, both of Belchertown; D. Joseph Jerry, Shutesbury, all of MA (US)

(73) Assignee: University of MMassachusetts, Amherst, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/004,606

(22) Filed: Jan. 8, 1998

(Under 37 CFR 1.47)

Related U.S. Application Data

(63) Continuation-in-part of application No. 08/888,057, filed on Jul. 3, 1997, which is a continuation-in-part of application No. 08/781,752, filed on Jan. 10, 1997, now Pat. No. 5,945,577.

(51) Int. Cl.[7] ............................. C12N 15/00; A01K 67/00
(52) U.S. Cl. ................................ 800/24; 800/14; 800/15; 800/16; 800/17; 435/325
(58) Field of Search .................................. 800/24, 14, 15, 800/16, 17; 435/325

(56) References Cited

U.S. PATENT DOCUMENTS

| 4,994,384 | * | 2/1991 | Prather et al. | 435/172.3 |
| 5,057,420 | * | 10/1991 | Massey et al. | 435/172.3 |
| 5,945,577 | * | 8/1999 | Stice et al. | 800/24 |

FOREIGN PATENT DOCUMENTS

| WO 91/13150 | 9/1991 | (WO). |
| WO 94/29442 | 12/1994 | (WO). |
| WO 97/37009 | 10/1997 | (WO). |

OTHER PUBLICATIONS

Wilmut et al (1997) Nature 385, 810–813.*
Sims et al (1993) Proced. Natl. Acad. Sci. 90, 6143–6147.*
Campbell et al (1996) Nature 64–66.*
Schultz et al (1995) Seminars in Cell Biology 6, 201–208.*
Kappell et al (1992) Current Opinion in Biotechnology 3, 548–553.*
Wall (1996) Theriogenology 45, 57–68.*
Houdebine (1994) Journal of Biotechnology 34, 269–287.*
Mullins et al (1996) Journal of Clinical Investigation 98, S37–S40.*
Seamark (1994) Reproductive Fertility and Development 6, 653–657.*
Hyttinen et al (1994) Bio/Technology 12, 606–608.*
Sims et al (1993) Proced, Natl. Acad. Sci. 90, 6143–6147.*
Donkin et al (1993) J. Animal Sci. 71, 2218–2227.*
Lovell–Badge et al, Cold Spring Harbor Symp. Quant. Biol, vol. 50, pp. 707–711, Cold Spring Harbor Laboratory Press, Cold Spring Harbor, New York, 1985.*
Fulka et al (1998) BioEssays 20, 847–851.*
Kono (1997) Rev. Reprod. 2, 74–80.*
First et al, Systems for Production of Calves from Cultured Bovine Embryonic Cells, *Reproduction, Fertility, and Development*, vol. 6, pp 553–562 (1994).
Bartlett et al, Evaluation of extracellular matrices and the plasminogen activator system in sheep inner cell mass and trophectodermal outgrowth in vitro, *Biology of Reproduction*, vol. 52, pp 1426–1445 (1995).
Talbot et al, In vitro pluripotency of epiblasts derived from bovine blastocytes, *Molecular Reproduction and Development*, vol. 42, pp 35–52 (1995).
Talbot et al, Culturing the epiblast cells of the pig blastocyst. *In Vitro Cellular and Development Biology*, vol. 29A, pp. 543–554 (Jul. 1993).
Annelies et al, Isolation and Characterization of Permanent Cell Lines from Inner Cell Mass Cells of Bovine Blastocysts, *Molecular Reproduction and Development*, vol. 40, pp 444–454 (1995).
Collas et al, Nuclear Transplantation by Microinjection of Inner Cell Mass and Granulosa Cell Nuclei, *Molecular Reproduction and Development*, vol. 38, pp. 264–267 (1994).
Sims et al, Production of calves by transfer of nuclei from cultured inner cell mass cells, *Proceedings of the National Academy of Sciences, USA*, vol. 90, pp 6143–6147 (Jun. 1993).
Callard, R. et al., (1994), *The Cytokine Facts Book*, Academic Press, pp. 163–167.
Talbot et al. (1993), *In vitro Cellular and Development Biology* 29A, pp. 543–554.
Seamark et al., (1994), *Reproduction Fertility and Development* 6, pp. 653–657.
Bradley et al., (1992), *BioTechnology* 10, pp. 534–539.
Kappel et al. (1992), *Current Opinion in Biotechnology* 3, pp. 548–553.
Sims et al., (1994) *Proc. Natl. Acad. Sci. USA* 91, pp. 6143–6147.
Stice et al., "Pluripotent Bovine Embryonic Cell Lines Direct Embryonic Development Following Nuclear Transfer", *Biology of Reproduction*, vol. 54, No. 1, Jan. 1996, pp. 100–110.
Cibelli J.B. et al., "Production of germline chimeric bovine fetuses from transgenic enbryonic stem cells", *Theriogenology*, vol. 47, No. 1, Jan. 1997, p. 241.

* cited by examiner

*Primary Examiner*—Deborah Crouch
(74) *Attorney, Agent, or Firm*—Robin L. Teskin

(57) ABSTRACT

Methods and cell lines for cloning bovine embryos and offspring are provided. The resultant embryos or offspring are especially useful for the expression of desired heterologous DNAs.

23 Claims, No Drawings

CLONING USING DONOR NUCLEI FROM A NON-QUIESECENT SOMATIC CELLS

CROSS-REFERENCE TO RELATED APPLICATIONS

This application is a continuation-in-part of Ser. No. 08/888,057, filed Jul. 3, 1997, which is a continuation-in-part of Ser. No. 08/781,752, filed Jan. 10, 1997, now U.S. Pat. No. 5,945,577, the contents of which are hereby incorporated by reference.

FIELD OF THE INVENTION

The present invention relates to cloning procedures in which cell nuclei derived from differentiated fetal or adult bovine cells, which include non-serum starved differentiated fetal or adult bovine cells, are transplanted into enucleated oocytes of the same species as the donor nuclei. The nuclei are reprogrammed to direct the development of cloned embryos, which can then be transferred to recipient females to produce fetuses and offspring, or used to produce cultured inner cell mass cells (CICM). The cloned embryos can also be combined with fertilized embryos to produce chimeric embryos, fetuses and/or offspring.

REFERENCES

The following publications, patent applications and patents are cited in this application as superscript numbers:

1 Bain, et al., *Dev. Biol.* 168:342–357 (1995)
2 Bradley, et al., *Nature* 309:255–256 (1984)
3 Campbell, et al., *Theriogenology* 43:181 (1995)
4 Campbell, et al., *Nature* 380:64–68 (1996)
5 Cherny, et al., *Theriogenology* 41:175 (1994)
6 Cheong, et al., *Biol. Reprod.* 48:958 (1993)
7 Collas and Barnes, *Mol. Reprod. Dev.* 38:264–267 (1994)
8 Cundiff, L. V., Bishop M. D. and Johnson, R. K. Challenges and opportunities for integrating genetically modified animals into traditional animal breeding plans. *Journal of Animal Science* 71(Suppl.3) 20–25 (1993).
9 Doetschman, T., Gene transfer in embryonic stem cells. In Pinkert. C. (ed.) *Transgenic Animal Technology: A Laboratory Handbook*. Academic Press, Inc., New York, pp. 115–146 (1994).
10 Evans, et al., *Nature* 29:154–156 (1981)
11 Fissore, et al., *Mol. Reprod. Dev.* 46:176–189 (1997)
12 Friedrich, G. and Soriano, P., Promoter traps in embyronic stem cells: A genetic screen to identify and mutate developmental genes in mice. *Genes and Development* 5:1513–1523 (1991).
13 Gerfen, et al., *Anim. Biotech.* 6(1):1–14 (1995)
14 Graham, *Wister Inot. Symp. Monogr.* 9:19 (1969)
15 Handyside, et al., *Roux's Arch. Dev. Biol.* 196:185–190 (1987)
16 Keefer, et al., *Biol. Reprod.* 50:935–939 (1994)
17 MacQuitty, *Nature Biotech.* 15:294 (1987)
18 Martin, *Proc. Natl. Acad. Sci., USA* 78:7634–7638 (1981)
19 Notarianni, et al., *J. Reprod. Fert. Suppl.* 41:51–56 (1990)
20 Notarianni, et al., *J. Reprod. Fert. Suppl.* 43:255–260 (1991)
21 Palacios, et al., *Proc. Natl. Acad. Sci., USA* 92:7530–7537 (1995)
22 Pedersen, *J. Reprod. Fertil. Dev.* 6:543–552 (1994)
23 Prather, et al., *Differentiation* 48:1–8 (1991)
24 Purcel, V. G. and Rexroad, Jr., C. E., Status of research with transgenic farm animals, *Journal of Animal Science* 71(Suppl.3). 10–19 (1993).
25 Saito, et al., *Roux's Arch. Dev. Biol.* 201:134–141 (1992)
26 Seidel, G. E., Jr., Resource requirements for transgenic livestock research. *Journal of Animal Science* 71(Suppl. 3). 26–33 (1993).
27 Sims, et al., *Proc. Natl. Acad. Sci., USA* 90:6143–6147 (1993)
28 Smith, et al., *Dev. Biol.* 121:1–9 (1987)
29 Smith, et al., *Biol. Reprod.* 40:1027–1035 (1989)
30 Stice and Robl, *Mol. Reprod. Dev.* 25:272–280 (1990)
31 Stice, et al., *Biol. Reprod.* 54:100–110 (1996)
32 Van Stekelenburg-Hamers, et al., *Mol. Reprod. Dev.* 40:444–454 (1995)
33 Wall, et al., Development of porcine ova that were centrifuged to permit visualization of pronuclei and nuclei, *Biol. Reprod.* 32:645–651 (1985)
34 Wilmut, I., Schnieke, A. E., McWhir, J., Kind, A. J., Campbell, K. H. S., Viable offspring derived from fetal and adult mammalian cells, *Nature* 385:810–813 (1997).
35 Evans, et al., WO 90/03432, published Apr. 5, 1990.
36 Smith, et al., WO 94/24274, published Oct. 27, 1994.
37 Wheeler, et al., WO 94/26884, published Nov. 24, 1994.
38 Prather, et al., U.S. Pat. No. 4,994,384, issued Feb. 19, 1991.
39 Wheeler, U.S. Pat. No. 5,057,420, issued Oct. 15, 1991.
40 Rosenkrans, Jr., et al., U.S. Pat. No. 5,096,822, issued Mar. 17, 1992.

All of the above publications, patent applications and patents are herein incorporated by reference in their entirety to the same extent as if each individual publication, patent application or patent was specifically and individually indicated to be incorporated by reference in its entirety.

BACKGROUND OF THE INVENTION

Genetic modification of cattle could be useful in increasing the efficiency of meat and milk production. An ideal system for producing transgenic animals for agricultural applications would be highly efficient and use small numbers of recipient animals to produce transgenics. It would allow the insertion of a transgene into a specific genotype. The insertion would preferably be into a predetermined site which would confer high expression and not affect general viability and productivity of the animal. Furthermore, the identification of a locus for insertion would allow multiple lines to be produced and crossed to produce homozygotes and new genetic background could easily be added to the transgenic line by the production of new transgenics at any time. Therefore, the ideal system would likely require the transfection and selection of cells that could be easily grown in culture yet retain the potency to form germ cells and pass the gene to subsequent generations.

Various methods have been utilized in an attempt to genetically modify cattle so as to introduce superior agricultural qualities including pronuclear microinjection. One of the limitations of pronuclear microinjection is that the gene insertion site is random. This typically results in variations in expression levels and several transgenic lines must be produced to obtain one line with appropriate levels of expression to be useful. Because integration is random, it is advantageous that a line of transgenic animals be started from one founder animal, to avoid difficulties in monitoring zygosity and potential difficulties that might occur with interactions among multiple insertion sites.[8] Furthermore, starting a transgenic line from one hemizygous animal with a random insert would require breeding several generations and significant time for introgression of the transgene into the population before breeding and testing homozygotes if inbreeding is to be avoided.[8] Even without concern for inbreeding, it would take 6.5 years before reproduction could be tested in homozygous animals.[26] Finally, the quality of the genetics of a monozygous transgenic line would lag behind that of the general population because of the reduced population within which to select future generations of transgenic animals and the difficulty of bringing new genetics into a population in which the transgene is fixed.

A second limitation of the pronuclear microinjection procedure is its efficiency; which ranges from 0.34 to 2.63% of the gene-injected embryos developing into transgenic animals and a fraction of these appropriately expressing the gene.[24] This inefficiency results in a high cost of producing transgenic cattle because of the large number of recipients needed and, more importantly, unpredictability in the genetic background into which the gene is inserted because of the large number of embryos needed for microinjection. For agricultural purposes, a high quality genetic background is essential, therefore, long-term backcrossing strategies must be used with pronuclear microinjection. Thus, the ability to clone, or to make numerous identical genetic copies, of an animal comprising a desired genetic modification would be advantageous.

Another such system for producing transgenic animals has been developed and widely used in the mouse and involves the use of embryonic stem (ES) cells.

Embryonic stem cells in mice have enabled researchers to select for transgenic cells and perform gene targeting. This allows more genetic engineering than is possible with other transgenic techniques. Mouse ES cells are relatively easy to grow as colonies in vitro. The cells can be transfected by standard procedures and transgenic cells clonally selected by antibiotic resistance.[9] Furthermore, the efficiency of this process is such that sufficient transgenic colonies (hundreds to thousands) can be produced to allow a second selection for homologous recombinants.[9] Mouse ES cells can then be combined with a normal host embryo and, because they retain their potency, can develop into all the tissues in the resulting chimeric animal, including the germ cells. The transgenic modification can then be transmitted to subsequent generations.

Methods for deriving embryonic stem (ES) cell lines in vitro from early preimplantation mouse embryos are well known.[10,18] ES cells can be passaged in an undifferentiated state, provided that a feeder layer of fibroblast cells[10] or a differentiation inhibiting source[28] is present.

ES cells have been previously reported to possess numerous applications. For example, it has been reported that ES cells can be used as an in vitro model for differentiation, especially for the study of genes which are involved in the regulation of early development. Mouse ES cells can give rise to germline chimeras when introduced into preimplantation mouse embryos, thus demonstrating their pluripotency.[2]

In view of their ability to transfer their genome to the next generation, ES cells have potential utility for germline manipulation of livestock animals by using ES cells with or without a desired genetic modification. Some research groups have reported the isolation of purportedly pluripotent embryonic cell lines. For example, Notarianni, et al.[20] reports the establishment of purportedly stable, pluripotent cell lines from pig and sheep blastocysts which exhibit some morphological and growth characteristics similar to that of cells in primary cultures of inner cell masses isolated immunosurgically from sheep blastocysts. Also, Notarianni, et al.[19] discloses maintenance and differentiation in culture of putative pluripotential embryonic cell lines from pig blastocysts. Gerfen, et al.[13] discloses the isolation of embryonic cell lines from porcine blastocysts. These cells are stably maintained without mouse embryonic fibroblast feeder layers and reportedly differentiate into several different cell types during culture.

Further, Saito, et al.[25] reports cultured, bovine embryonic stem cell-like cell lines which survived three passages, but were lost after the fourth passage. Handyside, et al.[15] discloses culturing of immunosurgically isolated inner cell masses of sheep embryos under conditions which allow for the isolation of mouse ES cell lines derived from mouse ICMs. Handyside, et al. also reports that under such conditions, the sheep ICMs attach, spread, and develop areas of both ES cell-like and endoderm-like cells, but that after prolonged culture only endoderm-like cells are evident.

Recently, Cherny, et al.[5] reported purportedly pluripotent bovine primordial germ cell-derived cell lines maintained in long-term culture. These cells, after approximately seven days in culture, produced ES-like colonies which stained positive for alkaline phosphatase (AP), exhibited the ability to form embryoid bodies, and spontaneously differentiated into at least two different cell types. These cells also reportedly expressed mRNA for the transcription factors OCT4, OCT6 and HES1, a pattern of homeobox genes which is believed to be expressed by ES cells exclusively.

Also recently, Campbell, et al.[4] reported the production of live lambs following nuclear transfer of cultured embryonic disc (ED) cells from day nine ovine embryos cultured under conditions which promote the isolation of ES cell lines in the mouse. The authors concluded that ED cells from day nine ovine embryos are totipotent by nuclear transfer and that totipotency is maintained in culture.

Van Stekelenburg-Hamers, et al.[32] reported the isolation and characterization of purportedly permanent cell lines from inner cell mass cells of bovine blastocysts. The authors isolated and cultured ICMs from 8 or 9 day bovine blastocysts under different conditions to determine which feeder cells and culture media are most efficient in supporting the attachment and outgrowth of bovine ICM cells. They concluded that the attachment and outgrowth of cultured ICM cells is enhanced by the use of STO (mouse fibroblast) feeder cells (instead of bovine uterus epithelial cells) and by the use of charcoal-stripped serum (rather than normal serum) to supplement the culture medium. Van Stekelenburg, et al. reported, however, that their cell lines resembled epithelial cells more than pluripotent ICM cells.

Smith, et al.[36], Evans, et al.[35], and Wheeler, et al.[37] report the isolation, selection and propagation of animal stem cells which purportedly may be used to obtain transgenic animals. Evans, et al. also reported the derivation of purportedly pluripotent embryonic stem cells from porcine and bovine species which assertedly are useful for the production of transgenic animals. Further, Wheeler, et al. disclosed embryonic stem cells which are assertedly useful for the manufacture of chimeric and transgenic ungulates.

Alternatively, ES cells from a transgenic embryo could be used in nuclear transplantation. The use of ungulate inner cell mass (ICM) cells for nuclear transplantation has also been reported. In the case of livestock animals, e.g., ungulates, nuclei from like preimplantation livestock embryos support the development of enucleated oocytes to term.[16,29] This is in contrast to nuclei from mouse embryos which beyond the eight-cell stage after transfer reportedly do not support the development of enucleated oocytes.[6] Therefore, ES cells from livestock animals are highly desirable because they may provide a potential source of totipotent donor nuclei, genetically manipulated or otherwise, for nuclear transfer procedures. Collas, et al.[7] discloses nuclear transplantation of bovine ICMs by microinjection of the lysed donor cells into enucleated mature oocytes. Collas, et al. disclosed culturing of embryos in vitro for seven days to produce fifteen blastocysts which, upon transferral into bovine recipients, resulted in four pregnancies and two births. Also, Keefer, et al.[27] disclosed the use of bovine ICM cells as donor nuclei in nuclear transfer procedures, to produce blastocysts which, upon transplantation into bovine recipients, resulted in several live offspring. Further, Sims, et al.[27] disclosed the production of calves by transfer of nuclei from short-term in vitro cultured bovine ICM cells into enucleated mature oocytes.

Thus, based on the foregoing, it is evident that many groups have attempted to produce ES cell lines, e.g., because of their potential application in the production of cloned or transgenic embryos and in nuclear transplantation.

However, embryonic stem cell lines and other embryonic cell lines must be maintained in an undifferentiated state that requires feeder layers and/or the addition of cytokines to media. Even if these precautions are followed, these cells often undergo spontaneous differentiation and cannot be used to produce transgenic offspring by currently available methods. Also, some embryonic cell lines have to be propagated in a way that is not conducive to gene targeting procedures. Thus, genetic modification using differentiated cells would be advantageous.

The production of live lambs following nuclear transfer of cultured embryonic disc cells has also been reported.[4] Still further, the use of bovine pluripotent embryonic cells in nuclear transfer and the production of chimeric fetuses has been reported[7,31] Collas, et al.[7] demonstrated that granulosa cells (adult cells) could be used in a bovine cloning procedure to produce embryos. However, there was no demonstration of development past early embryonic stages (blastocyst stage). Also, granulosa cells are not easily cultured and are only obtainable from females. Collas, et al.[7] did not attempt to propagate the granulosa cells in culture or try to genetically modify those cells. Wilmut, et al.[34] produced nuclear transfer sheep offspring derived from fetal fibroblast cells, and one offspring from a cell derived from an adult sheep.

Cloning sheep cells is easier in comparison with cells of other species. This phenomenon is illustrated by the following table:

| SPECIES (from hardest to easiest to clone) | CELL TYPE CLONED | OFFSPRING PRODUCED |
| --- | --- | --- |
| Pig (Prather, Biol. Report, 41:414–418, 1989) | 2 and 4 cell stage embryo | yes |
| Pig (Prather, Id., 1989; | greater than 4 cell stage | no |
| Mouse (Cheong, et al., Biol. Reprod., 48:958–963, 1993) | 2, 4 and 8 cell stage embryo | yes |
| Mouse (Tsunoda, et al., J. Reprod. Fertil., 98:537–540, 1993) | greater than 8 cell stage | no |
| Cattle (Keefer, et al., Biol. Reprod., 50:935–939, 1994) | 64 to 128 cell stage (ICM) | yes |
| Cattle (Stice, et al., Biol. Repro., 54:100–110, 1996) | embryonic cell line from ICM | no |
| Sheep (Campbell, et al., Nature, 380:64–66, 1996) | embryonic cell line from ICM | yes |
| Sheep (Wilmut, et al., BARC Symposia, 20:145–150, 1997) | fetal and adult cells | yes |

However, there exist problems in the area of producing transgenic cows. By current methods, heterologous DNA is introduced into either early embryos or embryonic cell lines that differentiate into various cell types in the fetus and eventually develop into a transgenic animal. One limitation is that many early embryos are required to produce one transgenic animal and, thus, this procedure is very inefficient. Also, there is no simple and efficient method of selecting for a transgenic embryo before going through the time and expense of putting the embryos into surrogate females. In addition, gene targeting techniques cannot be easily accomplished with early embryo transgenic procedures.

Therefore, notwithstanding what has previously been reported in the literature, there exists a need for improved methods of cloning cows using cultured differentiated cells as donor nuclei.

OBJECTS AND SUMMARY OF THE INVENTION

It is an object of the invention to provide novel and improved methods for producing cloned cows using cultured differentiated bovine cells, in particular non-serum starved differentiated bovine cells as donor nuclei.

It is a more specific object of the invention to provide a novel method for cloning cows which involves transplantation of the nucleus of a differentiated cow cell, in particular a non-serum starved differentiated bovine cell, into an enucleated cow oocyte.

It is another object of the invention to provide a method for multiplying adult cows having proven genetic superiority or other desirable traits.

It is another object of the invention to provide an improved method for producing genetically engineered or transgenic cows (i.e., NT units, fetuses, offspring). The invention also provides genetically engineered or transgenic cows, including those made by such a method.

It is a more specific object of the invention to provide a method for producing genetically engineered or transgenic cows by which a desired DNA sequence is inserted, removed or modified in a differentiated cow cell or cell nucleus, which may be non-serum starved, prior to use of that differentiated cell or cell nucleus for formation of a NT unit. The invention also provides genetically engineered or transgenic cows made by such a method.

It is another object of the invention to provide a novel method for producing cow CICM cells which involves transplantation of a nucleus of a serum or non-serum starved differentiated cow cell into an enucleated cow oocyte, and then using the resulting NT unit to produce CICM cells. The invention also provides cow CICM cells produced by such a method.

It is another object of the invention to use such cow CICM cells for therapy or diagnosis.

It is a specific object of the invention to use such cow CICM cells for treatment or diagnosis of any disease wherein cell, tissue or organ transplantation is therapeutically or diagnostically beneficial. The CICM cells may be used within the same species or across species.

It is another object of the invention to use cells or tissues derived from cow NT units, fetuses or offspring for treatment or diagnosis of any disease wherein cell, tissue or organ transplantation is therapeutically or diagnostically beneficial. Such diseases and injuries include Parkinson's, Huntington's, Alzheimer's, ALS, spinal cord injuries, multiple sclerosis, muscular dystrophy, diabetes, liver diseases, heart disease, cartilage replacement, burns, vascular diseases, urinary tract diseases, as well as for the treatment of immune defects, bone marrow transplantation, cancer, among other diseases. The tissues may be used within the same species or across species.

It is another specific object of the invention to use cells or tissues derived from cow NT units, fetuses or offspring, or cow CICM cells produced according to the invention for the production of differentiated cells, tissues or organs.

It is another specific object of the invention to use cells or tissues derived from cow NT units, fetuses or offspring, or cow CICM cells produced according to the invention in vitro, e.g. for study of cell differentiation and for assay purposes, e.g. for drug studies.

It is another object of the invention to use cells, tissues or organs produced from such tissues derived from cow NT units, fetuses or offspring, or cow CICM cells to provide improved methods of transplantation therapy. Such therapies include by way of example treatment of diseases and injuries including Parkinson's, Huntington's, Alzheimer's, ALS, spinal cord injuries, multiple sclerosis, muscular dystrophy, diabetes, liver diseases, heart disease, cartilage replacement, burns, vascular diseases, urinary tract diseases, as well as for the treatment of immune defects, bone marrow transplantation, cancer, among other diseases.

It is another object of the invention to provide genetically engineered or transgenic tissues derived from cow NT units, fetuses or offspring, or cow CICM cells produced by inserting, removing or modifying a desired DNA sequence in a differentiated cow cell or cell nucleus prior to use of that differentiated cell or cell nucleus for formation of a NT unit.

It is another object of the invention to use the transgenic or genetically engineered tissues derived from cow NT units, fetuses or offspring, or cow CICM cells produced according to the invention for gene therapy, in particular for the treatment and/or prevention of the diseases and injuries identified, supra.

It is another object of the invention to use the tissues derived from cow NT units, fetuses or offspring, or cow CICM cells produced according to the invention, or transgenic or genetically engineered tissues derived from cow NT units, fetuses or offspring, or cow CICM cells produced according to the invention as nuclear donors for nuclear transplantation.

It is another object of the invention to use transgenic or genetically engineered cow offspring produced according to the invention in order to produce pharmacologically important proteins.

Thus, in one aspect, the present invention provides a method for cloning a cow (e.g., embryos, fetuses, offspring). The method comprises:

(i) inserting a desired serum or non-serum starved differentiated cow cell or cell nucleus into an enucleated cow oocyte, under conditions suitable for the formation of a nuclear transfer (NT) unit to yield a fused NT unit;

(ii) activating the fused NT unit to yield an activated NT unit; and (iii) transferring said activated NT unit to a host cow such that the NT unit develops into a fetus.

Optionally, the activated nuclear transfer unit is cultured until greater than the 2-cell developmental stage.

The cells, tissues and/or organs of the fetus are advantageously used in the area of cell, tissue and/or organ transplantation, or production of desirable genotypes.

The present invention also includes a method of cloning a genetically engineered or transgenic cow, by which a desired DNA sequence is inserted, removed or modified in the differentiated cow cell or cell nucleus prior to insertion of the differentiated cow cell or cell nucleus into the enucleated oocyte. Genetically engineered or transgenic cows produced by such a method are advantageously used in the area of cell, tissue and/or organ transplantation, production of desirable genotypes, and production of pharmaceutical proteins.

Also provided by the present invention are cows obtained according to the above method, and offspring of those cows.

In another aspect, the present invention provides a method for producing cow CICM cells. The method comprises:

(i) inserting a desired serum or non-serum starved differentiated cow cell or cell nucleus into an enucleated cow oocyte, under conditions suitable for the formation of a nuclear transfer (NT) unit to yield a fused NT unit;

(ii) activating the fused NT unit to yield an activated NT unit; and (iii) culturing cells obtained from said activated NT unit to obtain cow CICM cells.

Optionally, the activated nuclear transfer unit is cultured until greater than the 2-cell developmental stage.

The cow CICM cells are advantageously used in the area of cell, tissue and organ transplantation.

With the foregoing and other objects, advantages and features of the invention that will become hereinafter apparent, the nature of the invention may be more clearly understood by reference to the following detailed description of the preferred embodiments of the invention and to the appended claims.

DETAILED DESCRIPTION OF THE INVENTION

This invention provides improved to cloning procedures in which cell nuclei derived from differentiated fetal or adult bovine cells which may be serum or non-serum starved are transplanted into enucleated oocytes of the same species as the donor nuclei. However, prior to discussing this invention in further detail, the following terms will first be defined.

Definitions

As used herein, the following terms have the following meanings:

The term "differentiated" refers to cells having a different character or function from the surrounding structures or from the cell of origin. Differentiated cow cells are those cells which are past the early embryonic stage. More particularly, the differentiated cells are those from at least past the embryonic disc stage (day 10 of bovine embryogenesis). The differentiated cells may be derived from ectoderm, mesoderm or endoderm.

The term "nuclear transfer" or "nuclear transplantation" refers to a method of cloning wherein the nucleus from a donor cell is transplanted into enucleated oocytes. Nuclear transfer techniques or nuclear transplantation techniques are known in the literature.[3,7,16,27,35–37] Also, U.S. Pat. Nos.

4,994,384 and 5,057,420 describe procedures for bovine nuclear transplantation. In the subject application, nuclear transfer or nuclear transplantation or NT are used interchangeably.

The term "nuclear transfer unit" or "NT unit" refers to the product of fusion between a differentiated cow cell or cell nucleus and an enucleated cow oocyte, and is sometimes referred to herein as a fused NT unit.

The term "non-serum starved bovine differentiated cells" refers to cells cultured in the presence of serum greater than about 1%.

The term "fetus" refers to the unborn young of a viviparous animal after it has taken form in the uterus. In cows, the fetal stage occurs from 35 days after conception until birth.

The term "adult" refers to a mammal from birth until death.

According to the invention, cell nuclei derived from differentiated cow cells are transplanted into enucleated cow oocytes. The nuclei are reprogrammed to direct the development of cloned embryos, which can then be transferred into recipient females to produce fetuses and offspring, or used to produce CICM cells. The cloned embryos can also be combined with fertilized embryos to produce chimeric embryos, fetuses and/or offspring.

Prior art methods have used embryonic cell types in cloning procedures. This includes work by Campbell, et al.[4] and Stice, et al.[31] In both of those studies, embryonic cell lines were derived from embryos of less than 10 days of gestation. In both studies, the cells were maintained on a feeder layer to prevent overt differentiation of the donor cell to be used in the cloning procedure. The present invention uses differentiated cells.

Adult cells and fetal fibroblast cells from a sheep have purportedly been used to produce sheep offspring.[34] However, of the mammalian species studied, cloning of sheep appears to be the easiest, and pig cloning appears to be the most difficult. The successful cloning of cows using differentiated cell types according to the present invention was quite unexpected.

Thus, according to the present invention, multiplication of superior genotypes of cows is possible. This will allow the multiplication of adult cows with proven genetic superiority or other desirable traits. Genetic progress will be accelerated in the cow. By the present invention, there are potentially billions of fetal or adult cow cells that can be harvested and used in the cloning procedure. This will potentially result in many identical offspring in a short period.

It was unexpected that cloned embryos with fetal or adult donor nuclei could develop to advanced embryonic and fetal stages. The scientific dogma has been that only early embryonic cell types could direct this type of development. It was unexpected that a large number of cloned embryos could be produced from fetal or adult cells. Also, the fact that new transgenic embryonic cell lines could be readily derived from transgenic cloned embryos was unexpected.

Adult cells and fetal fibroblast cells from a sheep have purportedly been used to produce a sheep offspring (Wilmut et al, 1997). In that study, however, it was emphasized that the use of a serum starved, nucleus donor cell in the quiescent state was important for success of the Wilmut cloning method. No such requirement for serum starvation or quiescence exists for the present invention. On the contrary, cloning is achieved using non-serum starved, differentiated mammalian cells. Moreover, cloning efficiency according to the present invention can be the same regardless of whether fetal or adult donor cells are used, whereas Wilmut et al (1997) reported that lower cloning efficiency was achieved with adult donor cells.

There has also been speculation that the Wilmut, et al. method will lead to the generation of transgenic animals.[17] However, there is no reason to assume, for example, that nuclei from adult cells that have been transfected with exogenous DNA will be able to survive the process of nuclear transfer. In this regard, it is known that the properties of mouse embryonic stem (ES) cells are altered by in vitro manipulation such that their ability to form viable chimeric embryos is effected. Therefore, prior to the present invention, the cloning of transgenic animals could not have been predicted.

The present invention also allows simplification of transgenic procedures by working with a cell source that can be clonally propagated. This eliminates the need to maintain the cells in an undifferentiated state, thus, genetic modifications, both random integration and gene targeting, are more easily accomplished. Also by combining nuclear transfer with the ability to modify and select for these cells in vitro, this procedure is more efficient than previous transgenic embryo techniques. According to the present invention, these cells can be clonally propagated without cytokines, conditioned media and/or feeder layers, further simplifying and facilitating the transgenic procedure. When transfected cells are used in cloning procedures according to the invention, transgenic cow embryos are produced which can develop into fetuses and offspring. Also, these transgenic cloned embryos can be used to produce CICM cell lines or other embryonic cell lines. Therefore, the present invention eliminates the need to derive and maintain in vitro an undifferentiated cell line that is conducive to genetic engineering techniques.

The present invention can also be used to produce cloned cow fetuses, offspring or CICM cells which can be used, for example, in cell, tissue and organ transplantation. By taking a fetal or adult cell from a cow and using it in the cloning procedure a variety of cells, tissues and possibly organs can be obtained from cloned fetuses as they develop through organogenesis. Cells, tissues, and organs can be isolated from cloned offspring as well. This process can provide a source of "materials" for many medical and veterinary therapies including cell and gene therapy.

If the cells are transferred back into the animal in which the cells were derived, then immunological rejection is averted. Also, because many cell types can be isolated from these clones, other methodologies such as hematopoietic chimerism can be used to avoid immunological rejection among animals of the same species as well as between species.

Thus, in one aspect, the present invention provides a method for cloning a cow. In general, the cow will be produced by a nuclear transfer process comprising the following steps:

(i) obtaining desired differentiated cow cells, which may be serum or non-serum starved, to be used as a source of donor nuclei;

(ii) obtaining oocytes from a cow;

(iii) enucleating said oocytes;

(iv) transferring the desired differentiated cell or cell nucleus into the enucleated oocyte, e.g., by fusion or injection, to form an NT unit;

(v) activating the NT unit to yield an activated NT unit; and (vii) transferring said activated NT unit to a host cow such that the NT unit develops into a fetus.

Optionally, the activated nuclear transfer unit is cultured until greater than the 2-cell developmental stage prior to transfer to the host cow.

The present invention also includes a method of cloning a genetically engineered or transgenic cow, by which a desired DNA sequence is inserted, removed or modified in the serum or non-serum starved differentiated cow cell or cell nucleus prior to insertion of the differentiated cow cell or cell nucleus into the enucleated oocyte.

Also provided by the present invention are cows obtained according to the above method, and offspring of those cows.

In addition to the uses described above, the genetically engineered or transgenic cows according to the invention can be used to produced a desired protein, such as a pharmacologically important protein, e.g., human serum albumin. That desired protein can then be isolated from the milk or other fluids or tissues of the transgenic cow. Alternatively, the exogenous DNA sequence may confer an agriculturally useful trait to the transgenic cow, such as disease resistance, decreased body fat, increased lean meat product, improved feed conversion, or altered sex ratios in progeny.

The present invention further provides for the use of NT fetuses and NT and chimeric offspring in the area of cell, tissue and organ transplantation.

In another aspect, the present invention provides a method for producing cow CICM cells. The method comprises:

(i) inserting a desired serum or non-serum starved differentiated cow cell or cell nucleus into an enucleated cow oocyte, under conditions suitable for the formation of a nuclear transfer (NT) unit;

(ii) activating the resultant nuclear transfer unit to yield an activated nuclear transfer unit; and (iii) culturing cells obtained from said activated NT unit to obtain cow CICM cells.

Optionally, the activated nuclear transfer unit is cultured until greater than the 2-cell developmental stage.

The cow CICM cells are advantageously used in the area of cell, tissue and organ transplantation, or in the production of fetuses or offspring, including transgenic fetuses or offspring.

Preferably, the NT units will be cultured to a size of at least 2 to 400 cells, preferably 4 to 128 cells, and most preferably to a size of at least about 50 cells.

Cow cells may be obtained by well known methods. Cow cells useful in the present invention include, by way of example, epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells, etc. Moreover, the cow cells used for nuclear transfer may be obtained from different organs, e.g., skin, lung, pancreas, liver, stomach, intestine, heart, reproductive organs, bladder, kidney, urethra and other urinary organs, etc. These are just examples of suitable donor cells. Suitable donor cells, i.e., cells useful in the subject invention, may be obtained from any cell or organ of the body. This includes all somatic or germ cells.

Fibroblast cells are an ideal cell type because they can be obtained from developing fetuses and adult cows in large quantities. Fibroblast cells are differentiated somewhat and, thus, were previously considered a poor cell type to use in cloning procedures. Importantly, these cells can be easily propagated in vitro with a rapid doubling time and can be clonally propagated for use in gene targeting procedures. Again the present invention is novel because differentiated cell types are used. The present invention is advantageous because the cells can be easily propagated, genetically modified and selected in vitro.

Other reported cloning methods (e.g., Wilmut et al, 1997) have relied on the use of serum starved cells. The present invention, however, includes the use of donor cells which are not in a state of serum starvation. According to Wilmut et al (1997), serum starved cells are quiescent, i.e., exiting the growth phase. Other methods (chemical, temperature, etc.) are also capable of producing quiescent cells. By contrast, in the present invention the donor cells used may or may not be quiescent.

The stage of maturation of the oocyte at enucleation and nuclear transfer has been reported to be significant to the success of NT methods. In general, successful mammalian embryo cloning practices use the metaphase II stage oocyte as the recipient oocyte because at this stage it is believed that the oocyte can be or is sufficiently "activated" to treat the introduced nucleus as it does a fertilizing sperm. In domestic animals, the oocyte activation period generally ranges from about 16–52 hours, preferably about 20–45 hours post-aspiration.

Methods for isolation of oocytes are well known in the art. Essentially, this will comprise isolating oocytes from the ovaries or reproductive tract of a bovine mammal, e.g., a bovine. A readily available source of bovine oocytes is slaughterhouse materials.

For the successful use of techniques such as genetic engineering, nuclear transfer and cloning, oocytes must generally be matured in vitro before these cells may be used as recipient cells for nuclear transfer, and before they can be fertilized by the sperm cell to develop into an embryo. This process generally requires collecting immature (prophase I) oocytes from mammalian ovaries, e.g., bovine ovaries obtained at a slaughterhouse, and maturing the oocytes in a maturation medium prior to fertilization or enucleation until the oocyte attains the metaphase II stage, which in the case of bovine oocytes generally occurs about 18–24 hours post-aspiration. For purposes of the present invention, this period of time is known as the "maturation period." As used herein for calculation of time periods, "aspiration" refers to aspiration of the immature oocyte from ovarian follicles.

Additionally, metaphase II stage oocytes, which have been matured in vivo have been successfully used in nuclear transfer techniques. Essentially, mature metaphase II oocytes are collected surgically from either non-superovulated or superovulated cows or heifers 35 to 48 hours past the onset of estrus or past the injection of human chorionic gonadotropin (hCG) or similar hormone.

The stage of maturation of the oocyte at enucleation and nuclear transfer has been reported to be significant to the success of NT methods. (See e.g., Prather et al., *Differentiation*, 48, 1–8, 1991). In general, successful mammalian embryo cloning practices use the metaphase II stage oocyte as the recipient oocyte because at this stage it is believed that the oocyte can be or is sufficiently "activated" to treat the introduced nucleus as it does a fertilizing sperm. In domestic animals, and especially cattle, the oocyte activation period generally ranges from about 16–52 hours, preferably about 28–42 hours post-aspiration.

For example, immature oocytes may be washed in HEPES buffered hamster embryo culture medium (HECM) as described in Seshagine et al., *Biol. Reprod.*, 40, 544–606, 1989, and then placed into drops of maturation medium consisting of 50 microliters of tissue culture medium (TCM) 199 containing 10% fetal calf serum which contains appropriate gonadotropins such as luteinizing hormone (LH) and follicle stimulating hormone (FSH), and estradiol under a layer of lightweight paraffin or silicon at 39° C.

After a fixed time maturation period, which ranges from about 10 to 40 hours, and preferably about 16–18 hours, the oocytes will be enucleated. Prior to enucleation the oocytes will preferably be removed and placed in HECM containing 1 milligram per milliliter of hyaluronidase prior to removal of cumulus cells. This may be effected by repeated pipetting through very fine bore pipettes or by vortexing briefly. The stripped oocytes are then screened for polar bodies, and the selected metaphase II oocytes, as determined by the presence of polar bodies, are then used for nuclear transfer. Enucleation follows.

Enucleation may be effected by known methods, such as described in U.S. Pat. No. 4,994,384 which is incorporated by reference herein. For example, metaphase II oocytes are either placed in HECM, optionally containing 7.5 micrograms per milliliter cytochalasin B, for immediate enucleation, or may be placed in a suitable medium, for example an embryo culture medium such as CR1aa, plus 10% estrus cow serum, and then enucleated later, preferably not more than 24 hours later, and more preferably 16–18 hours later.

Enucleation may be accomplished microsurgically using a micropipette to remove the polar body and the adjacent cytoplasm. The oocytes may then be screened to identify those of which have been successfully enucleated. This screening may be effected by staining the oocytes with 1 microgram per milliliter 33342 Hoechst dye in HECM, and then viewing the oocytes under ultraviolet irradiation for less than 10 seconds. The oocytes that have been successfully enucleated can then be placed in a suitable culture medium, e.g., CR1aa plus 10% serum.

In the present invention, the recipient oocytes will preferably be enucleated at a time ranging from about 10 hours to about 40 hours after the initiation of in vitro maturation, more preferably from about 16 hours to about 24 hours after initiation of in vitro maturation, and most preferably about 16–18 hours after initiation of in vitro maturation.

A single mammalian cell of the same species as the enucleated oocyte will then be transferred into the perivitelline space of the enucleated oocyte used to produce the NT unit. The mammalian cell and the enucleated oocyte will be used to produce NT units according to methods known in the art. For example, the cells may be fused by electrofusion. Electrofusion is accomplished by providing a pulse of electricity that is sufficient to cause a transient breakdown of the plasma membrane. This breakdown of the plasma membrane is very short because the membrane reforms rapidly. Thus, if two adjacent membranes are induced to breakdown and upon reformation the lipid bilayers intermingle, small channels will open between the two cells. Due to the thermodynamic instability of such a small opening, it enlarges until the two cells become one. Reference is made to U.S. Pat. No. 4,997,384 by Prather et al., (incorporated by reference in its entirety herein) for a further discussion of this process. A variety of electrofusion media can be used including e.g., sucrose, mannitol, sorbitol and phosphate buffered solution. Fusion can also be accomplished using Sendai virus as a fusogenic agent (Graham, *Wister Inot. Symp. Monogr.*, 9, 19, 1969).

Also, in some cases (e.g. with small donor nuclei) it may be preferable to inject the nucleus directly into the oocyte rather than using electroporation fusion. Such techniques are disclosed in Collas and Barnes, *Mol. Reprod. Dev.*, 38:264–267 (1994), incorporated by reference in its entirety herein.

Preferably, the bovine cell and oocyte are electrofused in a 500 μm chamber by application of an electrical pulse of 90–120V for about 15 μsec, about 24 hours after initiation of oocyte maturation. After fusion, the resultant fused NT units are then placed in a suitable medium until activation, e.g., CR1aa medium. Typically activation will be effected shortly thereafter, typically less than 24 hours later, and preferably about 4–9 hours later.

The NT unit may be activated by known methods. Such methods include, e.g., culturing the NT unit at subphysiological temperature, in essence by applying a cold, or actually cool temperature shock to the NT unit. This may be most conveniently done by culturing the NT unit at room temperature, which is cold relative to the physiological temperature conditions to which embryos are normally exposed.

Alternatively, activation may be achieved by application of known activation agents. For example, penetration of oocytes by sperm during fertilization has been shown to activate prefusion oocytes to yield greater numbers of viable pregnancies and multiple genetically identical calves after nuclear transfer. Also, treatments such as electrical and chemical shock may be used to activate NT embryos after fusion. Suitable oocyte activation methods are the subject of U.S. Pat. No. 5,496,720, to Susko-Parrish et al., herein incorporated by reference in its entirety.

Additionally, activation may be effected by simultaneously or sequentially:

(i) increasing levels of divalent cations in the oocyte, and (ii) reducing phosphorylation of cellular proteins in the oocyte.

This will generally be effected by introducing divalent cations into the oocyte cytoplasm, e.g., magnesium, strontium, barium or calcium, e.g., in the form of an ionophore. Other methods of increasing divalent cation levels include the use of electric shock, treatment with ethanol and treatment with caged chelators.

Phosphorylation may be reduced by known methods, e.g., by the addition of kinase inhibitors, e.g., serine-threonin kinase inhibitors, such as 6-dimethylaminopurine, staurosporine, 2-aminopurine, and sphingosine.

Alternatively, phosphorylation of cellular proteins may be inhibited by introduction of a phosphatase into the oocyte, e.g., phosphatase 2A and phosphatase 2B.

In one embodiment, NT activation is effected by briefly exposing the fused NT unit to a TL-HEPES medium containing 5 μM ionomycin and 1 mg/ml BSA, followed by washing in TL-HEPES containing 30 mg/ml BSA within about 24 hours after fusion, and preferably about 4 to 9 hours after fusion.

The activated NT units may then be cultured in a suitable in vitro culture medium until the generation of CICM cells and cell colonies. Culture media suitable for culturing and maturation of embryos are well known in the art. Examples of known media, which may be used for bovine embryo culture and maintenance, include Ham's F-10+10% fetal calf serum (FCS), Tissue Culture Medium-199 (TCM-199)+ 10% fetal calf serum, Tyrodes-Albumin-Lactate-Pyruvate (TALP), Dulbecco's Phosphate Buffered Saline (PBS), Eagle's and Whitten's media. One of the most common media used for the collection and maturation of oocytes is TCM-199, and 1 to 20% serum supplement including fetal calf serum, newborn serum, estrual cow serum, lamb serum or steer serum. A preferred maintenance medium includes TCM-199 with Earl salts, 10% fetal calf serum, 0.2 mM Na pyruvate and 50 pg/ml gentamicin sulphate. Any of the above may also involve co-culture with a variety of cell types such as granulosa cells, oviduct cells, BRL cells and uterine cells and STO cells.

Another maintenance medium is described in U.S. Pat. No. 5,096,822 to Rosenkrans, Jr. et al., which is incorporated herein by reference. This embryo medium, named CR1, contains the nutritional substances necessary to support an embryo.

CR1 contains hemicalcium L-lactate in amounts ranging from 1.0 mM to 10 mM, preferably 1.0 mM to 5.0 mM. Hemicalcium L-lactate is L-lactate with a hemicalcium salt incorporated thereon. Hemicalcium L-lactate is significant in that a single component satisfies two major requirements in the culture medium: (i) the calcium requirement necessary for compaction and cytoskeleton arrangement; and (ii) the lactate requirement necessary for metabolism and electron transport. Hemicalcium L-lactate also serves as valuable mineral and energy source for the medium necessary for viability of the embryos.

Advantageously, CR1 medium does not contain serum, such as fetal calf serum, and does not require the use of a co-culture of animal cells or other biological media, i.e., media comprising animal cells such as oviductal cells. Biological media can sometimes be disadvantageous in that they may contain microorganisms or trace factors which may be harmful to the embryos and which are difficult to detect, characterize and eliminate.

Examples of the main components in CR1 medium include hemicalcium L-lactate, sodium chloride, potassium chloride, sodium bicarbonate and a minor amount of fatty-acid free bovine serum albumin (Sigma A-6003). Additionally, a defined quantity of essential and non-essential amino acids may be added to the medium. CR1 with amino acids is known by the abbreviation "CR1aa."

CR1 medium preferably contains the following components in the following quantities:

sodium chloride—114.7 mM potassium chloride—3.1 mM sodium bicarbonate—26.2 mM hemicalcium L-lactate—5 mM fatty-acid free BSA—3 mg/ml In one embodiment, the activated NT embryos unit are placed in CR1aa medium containing 1.9 mM DMAP for about 4 hours followed by a wash in HECM and then cultured in CR1aa containing BSA.

For example, the activated NT units may be transferred to CR1aa culture medium containing 2.0 mM DMAP (Sigma) and cultured under ambient conditions, e.g., about 38.5° C., 5% $CO_2$ for a suitable time, e.g., about 4 to 5 hours.

Afterward, the cultured NT unit or units are preferably washed and then placed in a suitable media, e.g., CR1aa medium containing 10% FCS and 6 mg/ml contained in well plates which preferably contain a suitable confluent feeder layer. Suitable feeder layers include, by way of example, fibroblasts and epithelial cells, e.g., fibroblasts and uterine epithelial cells derived from ungulates, chicken fibroblasts, murine (e.g., mouse or rat) fibroblasts, STO and SI-m220 feeder cell lines, and BRL cells.

In one embodiment, the feeder cells comprise mouse embryonic fibroblasts. Preparation of a suitable fibroblast feeder layer is described in the example which follows and is well within the skill of the ordinary artisan.

The methods for embryo transfer and recipient animal management in the present invention are standard procedures used in the embryo transfer industry. Synchronous transfers are important for success of the present invention, i.e., the stage of the NT embryo is in synchrony with the estrus cycle of the recipient female. This advantage and how to maintain recipients are reviewed in Siedel, G. E., Jr. ("Critical review of embryo transfer procedures with cattle" in *Fertilization and Embryonic Development in Vitro* (1981) L. Mastroianni, Jr. and J. D. Biggers, ed., Plenum Press, New York, N.Y., page 323), the contents of which are hereby incorporated by reference.

The present invention can also be used to clone genetically engineered or transgenic cows. As explained above, the present invention is advantageous in that transgenic procedures can be simplified by working with a differentiated cell source that can be clonally propagated. In particular, the differentiated cells used for donor nuclei, which may or may not be serum-starved, have a desired DNA sequence inserted, removed or modified. Those genetically altered, differentiated cells are then used for nuclear transplantation with enucleated oocytes.

Any known method for inserting, deleting or modifying a desired DNA sequence from a mammalian cell may be used for altering the differentiated cell to be used as the nuclear donor. These procedures may remove all or part of a DNA sequence, and the DNA sequence may be heterologous. Included is the technique of homologous recombination, which allows the insertion, deletion or modification of a DNA sequence or sequences at a specific site or sites in the cell genome.

The present invention can thus be used to provide adult cows with desired genotypes. Multiplication of adult cows with proven genetic superiority or other desirable traits is particularly useful, including transgenic or genetically engineered animals, and chimeric animals. Thus, the present invention will allow production of single sex offspring, and production of cows having improved meat production, reproductive traits and disease resistance. Furthermore, cell and tissues from the NT fetus, including transgenic and/or chimeric fetuses, can be used in cell, tissue and organ transplantation for the treatment of numerous diseases as described below in connection with the use of CICM cells. Hence, transgenic cows have uses including models for diseases, xenotransplantation of cells and organs, and production of pharmaceutical proteins.

For production of CICM cells and cell lines, the activated NT units are cultured under conditions which promote cell division without differentiation to provide for cultured NT units. After cultured NT units of the desired size are obtained, the cells are mechanically removed from the zone and are then used. This is preferably effected by taking the clump of cells which comprise the cultured NT unit, which typically will contain at least about 50 cells, washing such cells, and plating the cells onto a feeder layer, e.g., irradiated fibroblast cells. Typically, the cells used to obtain the stem cells or cell colonies will be obtained from the inner most portion of the cultured NT unit which is preferably at least 50 cells in size. However, cultured NT units of smaller or greater cell numbers as well as cells from other portions of the cultured NT unit may also be used to obtain ES cells and cell colonies. The cells are maintained on the feeder layer in a suitable growth medium, e.g., alpha MEM supplemented with 10% FCS and 0.1 mM β-mercaptoethanol (Sigma) and L-glutamine. The growth medium is changed as often as necessary to optimize growth, e.g., about every 2–3 days.

This culturing process results in the formation of CICM cells or cell lines. One skilled in the art can vary the culturing conditions as desired to optimize growth of the particular CICM cells. Also, genetically engineered or transgenic cow CICM cells may be produced according to the present invention. That is, the methods described above can be used to produce NT units in which a desired DNA sequence or sequences have been introduced, or from which all or part of an endogenous DNA sequence or sequences have been removed or modified. Those genetically engineered or transgenic NT units can then be used to produce genetically engineered or transgenic CICM cells.

The resultant CICM cells and cell lines have numerous therapeutic and diagnostic applications. Most especially, such CICM cells may be used for cell transplantation therapies.

In this regard, it is known that mouse embryonic stem (ES) cells are capable of differentiating into almost any cell type, e.g., hematopoietic stem cells. Therefore, cow CICM cells produced according to the invention should possess similar differentiation capacity. The CICM cells according to the invention will be induced to differentiate to obtain the desired cell types according to known methods. For example, the subject cow CICM cells may be induced to differentiate into hematopoietic stem cells, neural cells, muscle cells, cardiac muscle cells, liver cells, cartilage cells, epithelial cells, urinary tract cells, neural cells, etc., by culturing such cells in differentiation medium and under conditions which provide for cell differentiation. Medium and methods which result in the differentiation of CICM cells are known in the art as are suitable culturing conditions.

For example, Palacios, et al.[21] teaches the production of hematopoietic stem cells from an embryonic cell line by subjecting stem cells to an induction procedure comprising initially culturing aggregates of such cells in a suspension culture medium lacking retinoic acid followed by culturing in the same medium containing retinoic acid, followed by transferral of cell aggregates to a substrate which provides for cell attachment.

Moreover, Pedersen[22] is a review article which references numerous articles disclosing methods for in vitro differentiation of embryonic stem cells to produce various differentiated cell types including hematopoietic cells, muscle, cardiac muscle, nerve cells, among others.

Further, Bain, et al.[1] teaches in vitro differentiation of embryonic stem cells to produce neural cells which possess neuronal properties. These references are exemplary of reported methods for obtaining differentiated cells from embryonic or stem cells. These references and in particular the disclosures therein relating to methods for differentiating embryonic stem cells are incorporated by reference in their entirety herein.

Thus, using known methods and culture mediums, one skilled in the art may culture the subject CICM cells, including genetically engineered or transgenic CICM cells, to obtain desired differentiated cell types, e.g., neural cells, muscle cells, hematopoietic cells, etc.

The subject CICM cells may be used to obtain any desired differentiated cell type. Therapeutic usages of such differentiated cells are unparalleled. For example, hematopoietic stem cells may be used in medical treatments requiring bone marrow transplantation. Such procedures are used to treat many diseases, e.g., late stage cancers such as ovarian cancer and leukemia, as well as diseases that compromise the immune system, such as AIDS. Hematopoietic stem cells can be obtained, e.g., by fusing adult somatic cells of a cancer or AIDS patient, e.g., epithelial cells or lymphocytes with an enucleated oocyte, obtaining CICM cells as described above, and culturing such cells under conditions which favor differentiation, until hematopoietic stem cells are obtained. Such hematopoietic cells may be used in the treatment of diseases including cancer and AIDS.

The present invention can be used to replace defective genes, e.g., defective immune system genes, or to introduce genes which result in the expression of therapeutically beneficial proteins such as growth factors, lymphokines, cytokines, enzymes, etc.

DNA sequences which may be introduced into the subject CICM cells include, by way of example, those which encode epidermal growth factor, basic fibroblast growth factor, glial derived neurotrophic growth factor, insulin-like growth factor (I and II), neurotrophin-3, neurotrophin-4/5, ciliary neurotrophic factor, AFT-1, cytokines (interleukins, interferons, colony stimulating factors, tumor necrosis factors (alpha and beta), etc.), therapeutic enzymes, etc.

The present invention includes the use of cow cells in the treatment of human diseases. Thus, cow CICM cells, NT fetuses and NT and chimeric offspring (transgenic or nontransgenic) may be used in the treatment of human disease conditions where cell, tissue or organ transplantation is warranted. In general, CICM cell, fetuses and offspring according to the present invention can be used within the same species (autologous, syngenic or allografts) or across species (xenografts). For example, brain cells from cow NT fetuses may be used to treat Parkinson's disease.

Also, the subject CICM cells, may be used as an in vitro model of differentiation, in particular for the study of genes which are involved in the regulation of early development. Also, differentiated cell tissues and organs using the subject CICM cells may be used in drug studies.

Further, the subject CICM cells may be used as nuclear donors for the production of other CICM cells and cell colonies.

In order to more clearly describe the subject invention, the following examples are provided.

EXAMPLES

Materials and Methods for Cow Cloning

Modified TL-Hepes-PVA Medium (Hepes-PVA)

| Component | Mol. Wt. | Conc. (mM) | g/l |
|---|---|---|---|
| NaCl | 58.45 | 114.00 | 6.6633 |
| KCl | 74.55 | 3.20 | 0.2386 |
| NaHCO$_3$ | 84.00 | 2.00 | 0.1680 |
| NaH$_2$PO$_4$ | 120.00 | 0.34 | 0.0408 |
| Na Lactate** | 112.10 | 10.00 | 1.868 ml |
| MgCl$_2$6H$_2$O | 203.30 | 0.50 | 0.1017 |
| CaCl$_2$2H$_2$O* | 147.00 | 2.00 | 0.2940 |
| Sorbitol | 182.20 | 12.00 | 2.1864 |
| HEPES | 238.30 | 10.00 | 2.3830 |
| Na Pyruvate | 110.00 | 0.20 | 0.0220 |
| Gentamycin | — | — | 500 µl |
| Penicillin G | — | — | 0.0650 |
| PVA | 10,000 | — | 0.1000 |

**60% syrup
*Add CaCl$_2$2H$_2$O last, slowly to prevent precipitation
Use 18 mohm, RO, DI water.
Adjust pH to 7.4, Check osmolarity and record.
Sterilize by vacuum filtration (0.22 µm), date and initial bottle.
Store at 4° C. and use within 10 days.

B$_2$ Medium

B$_2$ Medium is a ready-to-use synthetic medium conventionally used for cell culture, processing and handling of human sperm.

Composition:

Mineral Salts: KCl, NaCl, MGSO$_4$, NaHCO$_3$, Na$_2$HPO$_4$, KH$_2$PO$_4$.

Amino Acids: Asparagine, threonine, serine, glutamic acid, glycine, alanine, taurine, citrulline, valine, cystine, methionine, isoleucine, leucine, tyrosine, arginine, phenylalanine, ornithine, lysine, tryptophan, arginine, histidine, proline, and cysteine.

Albumin: 10 g/L Bovine serum albumin(BSA)
Lipid: Cholesterol
Sugars and metabolic by-products: Glucose, pyruvate, lactate, and acetate
Vitamins and ascorbic acid
Purine and pyrimidine bases
Antibiotics: 100 mg/liter of penicillin G and 40 mg/liter of streptomycin
Phenol Red: 15 milligrams/liter
pH: 7.2–7.5
Osmolarity: 275–305 mOsm/Kg
Antibiotic/Antimycotic (Ab/Am)
100 U/1 Penicillin, 100 µg/1 streptomycin and 0.25 µg/1 amphotericin B (Gibco #15240-062)
Add a 10 ml aliquot to each liter of saline.
Add 10 µl to each ml of semen.

Oocyte-Cumulus Complex (OCC) Collection

Ovaries are transported to the lab at 25° C. and immediately washed with 0.9% saline with antibiotic/antimycotic (10 ml/L; Gibco #600-5240g). Follicles between 3–6 mm are aspirated using 18 g needles and 50 ml Falcon tubes connected to vacuum system (GEML bovine system). After tube is filled, OCC's are allowed to settle for 5–10 minutes. Follicular fluid (bFF) is aspirated and saved for use in culture system if needed (see bFF preparation protocol below).

OCC Washing

OCCs are resuspended in 20 ml Hepes-PVA and allowed to settle; repeat 2 times. After last wash, OCCs are moved to grid dishes and selected for culture. Selected OCCs are washed twice in 60 mm dishes of Hepes-PVA. All aspiration and oocyte recovery are performed at room temperature (approx. 25° C.).

Isolation of Primary Cultures of Bovine Embryonic and Adult Fibroblast Cells

Primary cultures of bovine fibroblasts are obtained from cow fetuses 30 to 114 days postfertilization, preferably 45 days. The head, liver, heart and alimentary tract are aseptically removed, the fetuses minced and incubated for 30 minutes at 37° C. in prewarmed trypsin EDTA solution (0.05% trypsin/0.02% EDTA; GIBCO, Grand Island, N.Y.). Fibroblast cells are plated in tissue culture dishes and cultured in fibroblast growth medium (FGM) containing: alpha-MEM medium (BioWhittaker, Walkersville, Md.) supplemented with 10% fetal calf serum (FCS) (Hyclone, Logen, Utah), penicillin (100 IU/ml) and streptomycin (50 µl/ml). The fibroblasts are grown and maintained in a humidified atmosphere with 5% $CO_2$ in air at 37° C.

Adult fibroblast cells are isolated from the lung and skin of a cow. Minced lung tissue is incubated overnight at 10° C. in trypsin EDTA solution (0.05% trypsin/0.02% EDTA; GIBCO, Grand Island, N.Y.). The following day tissue and any disassociated cells are incubated for one hour at 37° C. in prewarmed trypsin EDTA solution and processed through three consecutive washes and trypsin incubations (one hr). Fibroblast cells are plated in tissue culture dishes and cultured in alpha-MEM medium (BioWhittaker, Walkersville, Md.) supplemented with 10% fetal calf serum (FCS) (Hyclone, Logen, Utah), penicillin (100 IU/ml) and streptomycin (50 Ml/ml). The fibroblast cells can be isolated at virtually any time in development, ranging from approximately post embryonic disc stage through adult life of the animal (bovine day 9 to 10 after fertilization to 5 years of age or longer).

Preparation of Fibroblast Cells for Nuclear Transfer

Examples of fetal fibroblasts which may be used as donor nuclei are:

1. Proliferating fibroblast cells that are not synchronized in any one cell stage or serum starved or quiescent can serve as nuclear donors. The cells from the above culture are treated for 10 minutes with trypsin EDTA and are washed three times in 100% fetal calf serum. Single cell fibroblast cells are then placed in micromanipulation drops of HbT medium (Bavister, et al., 1983). This is done 10 to 30 min prior to transfer of the fibroblast cells into the enucleated cow oocyte. Preferably, proliferating transgenic fibroblast cells having the CMV promoter and green fluorescent protein gene (9th passage) are used to produce NT units.

2. By a second method, fibroblast cells are synchronized in G1 or G0 of the cell cycle. The fibroblast cells are grown to confluence. Then the concentration of fetal calf serum in the FGM is cut in half over four consecutive days (day 0=10%, day 1=5%, day 2—2.5%, day 3=1.25%, day 4=0.625%. On the fifth day the cells are treated for 10 minutes with trypsin EDTA and washed three times in 100% fetal calf serum. Single cell fibroblasts are then placed in micromanipulation drops of HbT medium. This is done within 15 min prior to transfer of the fibroblast cells into the enucleated cow oocyte.

Removal of Cumulus Cells

After a maturation period, which ranges from about 30 to 50 hours, and preferably about 40 hours, the oocytes will be enucleated. Prior to enucleation the oocytes will preferably be removed and placed in HECM (Seshagiri and Bavister, 1989) containing 1 milligram per milliliter of hyaluronidase prior to removal of cumulus cells. This may be effected by repeated pipetting through very fine bore pipettes or by vortexing briefly (about 3 minutes). The stripped oocytes are then screened for polar bodies, and the selected metaphase II oocytes, as determined by the presence of polar bodies, are then used for nuclear transfer. Enucleation follows.

Example 1

Production of Transgenic Bovine Embryonic Stem Cells

The defining requirements we used for designating cells as ES cells were 1) the cells should be derived from the inner cell mass (ICM) of a blastocyst stage embryo; 2) they should be capable of dividing indefinitely in culture without showing signs of morphological differentiation; and 3) they should contribute to cells of the germ line and endodermal, mesodermal and ectodermal tissues when combined with a host embryo to form a chimera. In addition, cells were evaluated in relation to mouse ES cells for morphology, several cytoplasmic markers and growth characteristics.

Morphologically, the colonies that were established from bovine ICMs maintained distinct margins, had high nuclear to cytoplasmic ratios, generally maintained a high density of lipid granules and were cytokeratin and vimentin negative as in the mouse but, contrary to the mouse, were not positive for alkaline phosphatase. Another difference between mouse ES cells and bovine ES cells was that bovine ES cells were much slower growing than mouse ES cells indicating a much longer cell cycle (estimated to be about 40 hours).

Two methods were used to establish ES cell colonies from day 7 in vitro produced bovine blastocysts. The first method involved isolating the ICM immunosurgically. Anti-sera was developed against bovine spleen cells in mice. The zona pellucida was removed using 0.5% pronase until the zona thinned and could be removed by pipetting. The blastocysts were exposed to a 1:100 dilution of anti-bovine mouse serum for 45 minutes then washed and treated with guinea pig complement. The lysed trophectodermal cells were removed by pipetting. For the second method, the ICM was isolated mechanically using two 26 gauge needles. The needles were crossed and brought down on the zona intact blastocysts which were cut using a scissors action. Some of the trophectodermal cells remained with the ICM and inevitably disappeared following plating and passaging. An ES colony was considered established after the third passage without signs of differentiation. For the immunosurgically isolated ICMs 5/9 (55%) formed ES colonies and for the mechanically isolated ICMs 6/12 (50%) formed colonies. Because no difference was detected between these methods, the mechanical method was adopted for the advantage of simplicity.

Establishment of ES cell colonies and maintenance of the undifferentiated state depends on an intimate contact between the ICM and the leukemia inhibitory factor producing mouse fibroblast feeder layer. In an attempt to increase the contact during the initial establishment, day 7 in vitro produced ICMs were placed either beneath or on top of mouse fetal fibroblast feeder layers. As above, an ES colony was considered established after the third passage without signs of differentiation. In agreement with previous results 5/9 (55%) ICMs plated on top of the feeder layer produced colonies but only 4/11 (36%) of those placed beneath the feeder layer formed colonies. Apparently, placing the ICMs beneath the feeder layer did not provide the appropriate interaction to inhibit differentiation of the ICMs.

Several methods of passaging bovine ES cell colonies were attempted. Because it is beneficial to clonally propagate ES cells following transfection and is necessary for homologous recombination many attempts were made to trypsinize colonies to produce single cells and establish new colonies from these cells. To summarize, all attempts at clonally propagating bovine ES cells were unsuccessful. Therefore, the routine method of passage that was established was to mechanically cut the colony into pieces that contained at least 50 cells and plate the clumps of cells on new feeder layers.

Following the development of methods of establishing and passaging bovine ES cells and the identification of limitations in clonally propagating the cells we turned to pursuing methods of transfecting and selecting for transgenic cells. The construct that was used contained a human cytomegalovirus promoter and β-galactosidase/neomycin resistance fusion gene.[12] Selection was based on treatment with Geneticin (G418) to kill nonexpressing cells. The β-galactosidase gene was used to verify incorporation and expression.

Prior to transfecting cells, it was necessary to determine the sensitivity of nontransgenic cells to G418. Colonies from three different embryos were challenged with 0, 50, 100 and 150 $\mu g$ ml$^{-1}$ G418. A colony was considered dead when it completely lifted from the feeder layer. Survival varied among lines of cells with the first line surviving an average of 9 days at 100 $\mu m$ ml$^{-1}$ and 7 days at 150 Mg ml. The second line survived 12, 10 and 7 days at 50, 100 and 150 $\mu g$ ml$^{-1}$, respectively, and the third line survived 8, 7 and 5 days at 50, 100 and 150 $\mu g$ ml$^{-1}$, respectively. To ensure death of all nontransgenic colonies, 150 $\mu g$ ml$^{-1}$ G418 was chosen as the dose for subsequent transfection experiments.

Because it was not possible to trypsinize and produce a cell suspension of bovine ES cells, the method of transfection was limited to either microinjection or lipofection. Various lipofection protocols were tested and found to be effective on fibroblast and Comma D cell cultures but were not effective on bovine ES cells. Therefore, microinjection was used. ES cells from three different lines were microinjected into the nucleus with a linearized version of the construct described above. At one day following microinjection, the colonies were treated with 150 $\mu g$ ml$^{-1}$ G418 continuously for 30 days. For the three lines 3,753, 3,508 and 3,502 cells were injected and 5, 2 and 0 colonies, respectively, survived selection G418. Some cells within each of these colonies expressed β-galactosidase activity and samples of cells were positive for the transgene when amplified by PCR and analyzed by Southern blot hybridization. Because the colonies essentially disappeared during selection, it is likely that the transgenic lines were of clonal origin, although this was not confirmed. Variation in expression in cells within a colony was likely due to cell-to-cell variation in factors such as cell cycle state, position effects and others.

Potency of the cells was tested by producing chimeras with host embryos. Prior to evaluating the incorporation of ES cells into embryos, the relationship between the number of ES cells injected into morula and the rate of development to the blastocyst stage was investigated. As shown in table 1, either 4, 8 or 12 cells were injected. Rate of development to the blastocyst stage decreased with increasing number of ES cells used. As an injection control, fibroblasts, either 4, 8 or 12 cells, were injected into morula and as a noninjection control development of a group of nontreated embryos were culture to the blastocyst stage. There were no differences among the numbers of cells injected on development rate, but manipulation, or the injection of cells, did appear to have a detrimental effect on development. Although it was found that increasing the number of ES cells injected decreased the rate of development, it was also believed that decreasing the number of cells would decrease the level of chimerism in the embryos. A compromise of injection 8 cells was chosen for further experiments.

Incorporation of ES cells into bovine blastocysts was evaluated to determine if the ES cells could interact with the host embryo and be incorporated into the inner cell mass of the blastocyst. ES cells were labeled with 100 $\mu g$ ml$^{-1}$ of the fluorescent carbocyanine dye, DiI, then injected into morula stage embryos. Four days later, the resulting blastocysts were observed under the fluorescent microscope. Incorporation of labeled ES cells into both the ICM and the trophectoderm was detected in all blastocysts. To further verify that the cells were incorporated into the ICM, the trophectoderm was removed by immunosurgery and the isolated ICM was observed. In all cases, labeled cells were detected in the ICM. This indicated that the ES cells had appropriate cell surface molecules to be incorporated into the compacted morula and ICM and form the early precursors of the fetus.

The next step in examining the potency of the ES cells was to test chimerism in fetuses recovered at 40 days of gestation. Eighteen day 7 blastocysts, injected with 8 to 10 ES cells were transferred into six recipient cows. Forty days after transfer, the fetuses were recovered by Cesarean section. The total number of fetuses recovered was 12 with six being normally developing and 6 dead and in the process of being resorbed. Of the six normal fetuses, the β-GEO transgene was detected in some tissues in all of them (table 2). Of the abnormal fetuses, it was possible to analyze some tissues in one and it, too, was transgenic. In addition to analyzing somatic tissues, PGCs were isolated and analyzed in the normal fetuses and two showed evidence of transgenic cells. The results of this experiment indicated that the ES cells did have the capacity to differentiate into many different kinds of tissues, including germ cells, and survive at least 40 days in vivo.

Thus, the present invention provides a highly efficient method of producing pluripotent ES cells in the bovine. Bovine ES cells may be very useful as a source of in vitro produced cells for transplantation into humans.

Moreover, bovine cells are potentially useful for gene targeting.

TABLE 1

Effect of Cell Injection on Development of Bovine Morula to the Blastocyst Stage

| Type and Number of Cells Injected | Number of Cells Injected Blastocysts (%) | Number of Morula | Blastocyst (%) |
| --- | --- | --- | --- |
| ES 15 (24) | 4 | 62 | 15 (24) |
| ES 10 (15) | 8 | 65 | 10 (15) |
| ES 9 (13) | 12 | 67 | 9 (13) |
| Fib 16 (30) | 4 | 54 | 16 (30) |
| Fib 11 (19) | 8 | 58 | 11 (19) |
| Fib 10 (28) | 12 | 36 | 10 (28) |
| Control 19 (41) | 0 | 46 | 19 (41) |

TABLE 2

Contribution of Transgenic ES Cells to Various Tissues in 40-Day Bovine Fetuses

| Tissue | Fetus Number | | | | | |
| --- | --- | --- | --- | --- | --- | --- |
|  | 1 | 2 | 3 | 4 | 5 | 6 |
| Heart | + | + | − | + | + | + |
| Muscle | + | − | * | − | * | + |
| Brain | − | + | + | + | + | + |
| Liver | * | − | + | − | + | + |
| Gonads | − | + | + | + | + | + |
| PGC | + | − | + | − | − |  |
| CICM cell (also contributed to various tissues in the adult animal as shown in Table 4) | | | | | | |

*Not determined

Example 2

Isolation of Primary Cultures of Bovine Fetal and Adult Bovine Fibroblast Cells Primary cultures of bovine fibroblasts were obtained from fetuses (45 days of pregnancy). The head, liver, heart and alimentary tract were aseptically removed, the fetuses minced and incubated for 30 minutes at 37° C. in prewarmed trypsin EDTA solution (0.05% trypsin/0.02% EDTA; GIBCO, Grand Island, N.Y.). Fibroblast cells were plated in tissue culture dishes and cultured in alpha-MEM medium (BioWhittaker, Walkersville, Md.) supplemented with 10% fetal calf serum (FCS) (Hyclone, Logen, Utah), penicillin (100 IU/ml) and streptomycin (50 $\mu$l/ml). The fibroblasts were grown and maintained in a humidified atmosphere with 5% $CO_2$ in air at 37° C. Cells were passaged regularly upon reaching confluency.

Adult fibroblast cells were isolated from the lung and skin of a cow (approximately five years of age). Minced lung tissue was incubated overnight at 10° C. in trypsin EDTA solution (0.05% trypsin/0.02% EDTA; GIBCO, Grand Island, N.Y.). The following day tissue and any disassociated cells were incubated for one hour at 37° C. in prewarmed trypsin EDTA solution (0.05% trypsin/0.02% EDTA; GIBCO, Grand Island, N.Y.) and processed through three consecutive washes and trypsin incubations (one hr). Fibroblast cells were plated in tissue culture dishes and cultured in alpha-MEM medium (BioWhittaker, Walkersville, Md.) supplemented with 10% fetal calf serum (FCS) (Hyclone, Logen, Utah), penicillin (100 IU/ml) and streptomycin (50 $\mu$l/ml). The fibroblast cells can be isolated at virtually any time in development, ranging from approximately post embryonic disc stage through adult life of the animal (bovine day 12 to 15 after fertilization to 10 to 15 years of age animals). This procedure can also be used to isolate fibroblasts from other mammals, including mice.

Introduction of a Marker Gene (Foreign Heterologous DNA) Into Embryonic and Adult Fibroblast Cells The following electroporation procedure was conducted for both fetal and adult bovine fibroblast cells. Standard microinjection procedures may also be used to introduce heterologous DNA into fibroblast cells, however, in this example electroporation was used because it is an easier procedure.

Culture plates containing propagating fibroblast cells were incubated in trypsin EDTA solution (0.05% trypsin/0.02% EDTA; GIBCO, Grand Island, N.Y.) until the cells were in a single cell suspension. The cells were spun down at 500×g and re-suspended at 5 million cells per ml with phosphate buffered saline (PBS).

The reporter gene construct contained the cytomegalovirus promoter and the beta-galactosidase, neomycin phosphotransferase fusion gene (beta-GEO). The reporter gene and the cells at 40 $\mu$g/ml final concentration were added to the electroporation chamber. (500 V, ∞ Ohms, 0.4 cm electrode, 250 $\mu$F, 500 $\mu$L of cell suspension in DPBS) After the electroporation pulse, the fibroblast cells were transferred back into the growth medium (alpha-MEM medium) (BioWhittaker, Walkersville, Md.) supplemented with 10% fetal calf serum (FCS) (Hyclone, Logen, Utah), penicillin (100 IU/ml) and streptomycin (50 $\mu$l/ml).

The day after electroporation, attached fibroblast cells were selected for stable integration of the reporter gene. G418 (400 $\mu$g/ml) was added to growth medium for 15 days (range: 3 days until the end of the cultured cells' life span). This drug kills any cells without the beta-GEO gene, since they do not express the neo resistance gene. At the end of this time, colonies of stable transgenic cells were present. Each colony was propagated independently of each other. Transgenic fibroblast cells were stained with X-gal to observe expression of beta-galactosidase, and confirmed positive for integration using PCR amplification of the beta-GEO gene and run out on an agarose gel.

Use of Transgenic Fibroblast Cells in Nuclear Transfer Procedures to Create CICM Cell Lines and Transgenic Fetuses One line of cells (CL-1) derived from one colony of bovine fetal fibroblast cells was used as donor nuclei in the nuclear transfer (NT) procedure. General NT procedures are described above.

Slaughterhouse oocytes were matured in vitro. The oocytes were stripped of cumulus cells and enucleated with a beveled micropipette at approximately 18 to 20 hours post maturation (hpm). Enucleation was confirmed in TL-HEPES medium plus Hoechst 33342 (3 $\mu$g/ml; Sigma). Individual donor cells (fibroblasts) were then placed in the perivitelline space of the recipient oocyte. The bovine oocyte cytoplasm and the donor nucleus (NT unit) were fused together using electrofusion techniques. One fusion pulse consisting of 120 V for 15 μsec in a 500 μm gap chamber filled with fusion medium was applied to the NT unit. This occurred at 24 hpm. The NT units were placed in CR1aa medium until 26 to 27 hpm.

The general procedure used to artificially activate oocytes has been described above. NT unit activation was initiated between 26 and 27 hpm. Briefly, NT units were exposed for four minutes to ionomycin (5 μM; CalBiochem, La Jolla, Calif.) in TL-HEPES supplemented with 1 mg/ml BSA and then washed for five minutes in TL-HEPES supplemented with 30 mg/ml BSA. Throughout the ionomycin treatment, NT units were also exposed to 2 mM DMAP (Sigma). Following the wash, NT units were then transferred into a microdrop of CR1aa culture medium containing 2 mM DMAP (Sigma) and cultured at 38.5° C. and 5% $CO_2$ for four to five hours. The embryos were washed and then placed in CR1aa medium plus 10% FCS and 6 mg/ml BSA in four well plates containing a confluent feeder layer of mouse embryonic fibroblast. The NT units were cultured for three more days at 38.5° C. and 5% $CO_2$. Culture medium was changed every three days until days 5 to 8 after activation. At this time blastocyst stage NT embryos can be used to produce transgenic CICM (cultured inner cell mass) cell lines or fetuses. The inner cell mass of these NT units can be isolated and plated on a feeder layer. Also, NT units were transferred into recipient females. The pregnancies were aborted between 35–48 days of gestation. This resulted in seven cloned transgenic fetuses having the beta-GEO gene in all tissues checked. Six of the seven embryos had a normal heart beat detected via ultrasound observation. Also, histological sections of fetuses showed no overt anomalies. Thus, this is a fast and easy method of making transgenic CICM cell lines and fetuses. This procedure is generally conducive to gene targeted CICM cell lines and fetuses.

The table below summarizes the results of these experiments.

TABLE 3

| Donor Cell Type | n | Cleavage (%) | Blastocysts (%) | CICM* Lines (%) | Recovered Transgenic Fetuses (%) | Ongoing Pregnancies Past 40 Days |
|---|---|---|---|---|---|---|
| CL-1 bovine fetal fibroblast (bGEO) | 412 | 220 (53%) | 40 (10%) | 22 (55%) | N/A | N/A |
| CL-1 bovine fetal fibroblast (bGEO) | 3625 | 2127 (59%) | 46 (9%) | N/A | 7 fetuses† | 9‡ |
| CICM cell line derived from CL-1 NT embryos | 709 | | 5 (0.7%) | N/A | 0 | 6Δ |
| Adult bovine fibroblast | 648 | 331 (51%) | 43 (6.6%) | N/A | N/A | 1 |

*19 lines were positive for beta-GEO, 2 were negative and one line died prior to PCR detection.
†One fetus was dead and another was slightly retarded in development at 35 days of gestation. Five fetuses recovered between 38 to 45 days were normal. All fetuses were confirmed transgenic.
‡First offspring was born October 1997.
ΔTransgenic chimeric calf born cloned from this line of CICM cells (See Table 4), 6 transgenic chimeric offspring produced.

TABLE 4

| | Embryo-derived ES cells | | | | Fibroblast-derived ES cells | | | | | |
|---|---|---|---|---|---|---|---|---|---|---|
| Calf # | 901 | 902 | 903 | 904 | 907 | 908 | 909 | 910 | 911 | 912 |
| Skin | − | + | − | − | − | + | − | − | − | − |
| Muscle | + | − | + | − | + | − | − | − | − | + |
| Brain | − | − | − | + | − | + | + | + | + | − |
| Liver | − | − | − | + | − | − | − | − | − | − |
| Spleen | − | − | − | − | − | − | − | + | + | + |
| Kidney | − | − | − | − | − | − | − | − | − | − |
| Heart | − | − | − | + | − | − | − | − | − | − |
| Lung | − | − | + | − | − | − | − | − | − | − |
| Udder | − | + | + | − | − | − | − | − | − | − |
| Intestine | − | − | + | − | − | − | − | − | − | − |
| Ovary | na | − | na | na | na | − | na | − | − | − |
| Testicle | − | na | + | − | − | na | − | na | na | na |

Example 3

Production of Transgenic Cattle Somatic Cell Nuclear Transplant Embryos

Fibroblasts were chosen as the donor cell because of their ease of isolation, growth and transfection. Bovine fetal fibroblasts were produced from 30 to 100 mm crown rump length (approximately 40 to 80 days of gestation) fetuses obtained from the slaughterhouse. Fetuses were shipped by overnight express mail on ice. In some cases, when a two-day shipment was used, healthy fibroblast lines could still be produced. After propagation for three passages, fibroblasts were transfected by electroporation with a closed circular construct of $\mu$-GEO. Following electroporation, transfected cells were selected on 200 $\mu$g/ml of G418. After 10 to 15 days on selection, single colonies were isolated, propagated and used for nuclear transfer experiments.

Nuclear transplant blastocysts and fetuses were produced from fibroblasts using standard procedures. Basically, in vitro matured oocytes were obtained from Trans Ova Genetics, Inc. by overnight express mail. Oocytes were enucleated using fluorescent labeling of the DNA to verify enucleation. Trypsinized fibroblast cells were transferred to the perivitelline space and fused to the oocyte cytoplast by electroporation. Activation was induced by a combination of calcium ionophore and 6-dimethylaminopurine. The rate of development to the blastocyst stage was about 10% (353/3625) for nuclear transfer embryos and 14% (106/758) for activated controls. Some blastocysts were shipped to Ultimate Genetics, Inc. for transfer into recipient cows. Two blastocysts were transferred into each recipient. Fetuses recovered at day 40 were morphologically normal and fibroblast cells recovered from these fetuses expressed $\beta$-galactosidase at a high level. Development to term is in progress and few pregnancies have been lost beyond day 40 of gestation. One calf was born and several other pregnancies are due in 1998.

The results indicate that fibroblast nuclear transplantation should provide an ideal method of producing transgenic cattle. Transfection, selection and clonal propagation are relatively easy in primary fibroblasts. The CMV promoter, along with several other constitutive promoters, drive gene expression at a high rate in fibroblasts allowing for routine antibiotic selection. These factors have allowed us to produce a number of transgenic lines with high expressing random gene inserts. Our results also indicate that fibroblasts can be grown for a sufficient number of passages in vitro, without going senescent, to allow a second round of selection for a targeted insert. These results suggest that the fibroblast nuclear transplant system may be a method that will finally allow the commercial production of transgenic livestock for improved agricultural production.

Example 4

Bovine Chimeric Offspring Produced by Transgenic Embryonic Stem Cells Generated From Somatic Cell Nuclear Transfer Embryos Genetic modifications of bovine embryonic stem cells, particularly targeted integrations, would be of use for the production of transgenic cattle or for the production of in vitro derived tissues for transplantation into humans. Previous work in our laboratory indicated that bovine ES cells are slow growing and cannot be clonally propagated; limiting their usefulness for direct genetic modification. Therefore, an alternate approach for genetically modifying bovine ES cells was investigated. Somatic cells have been used in the past to generate bovine blastocysts (Collas and Barnes, *Mol. Reprod. Devel.*, 38:264–267; 1994) and may be used to produce ES cells. In this study, fetal fibroblasts were transfected then fused with enucleated oocytes to generate blastocysts and, subsequently, transgenic ES cells. The potency of these ES cells was then tested by their ability to form chimeric calves.

Fetal bovine fibroblasts were isolated from a 60 day fetus. Cells were stably transfected by electroporation with a cytomegalovirus promoter and a $\beta$-galactosidase/neomycin resistance fusion gene ($\beta$-Geo). After three weeks of negative cell selection on 400 $\mu$g/ml of Geneticin (Signa, St. Louis, Mo.), single transgenic colonies were isolated and determined positive for $\beta$-galactosidase activity and PCR analysis. Fibroblasts were grown on 150 $\mu$g/ml of Geneticin and, upon reaching 70 to 80% confluency, used for nuclear transplantation. Enucleated in vitro matured bovine oocytes were fused with actively dividing fibroblasts and chemically activated by ionomycin and 6-dimethylaminopurine. Following activation, embryos were cultured for 3 days in CR2 (Specialty Media, Lavallette, N.J.) with 1% fetal calf serum (FCS; HyClone, Logan, Utah) and mouse embryonic fibroblasts (MEF) as a co-culture, from day 4 to the blastocyst stage, embryos were cultured with 10% FCS. Thirty-seven nuclear transfer blastocysts out of 330 (11%) were produced and plated in MEF, 22 (60%) of those generated ES cell lines. Morphologically, these ES cells were similar to those described earlier (Cibelli et al, *Therio.*, 47:241; 1997), i.e., high nuclear/cytoplasmic ratio, the presence of lipid bodies and several nucleoli. In order to test the pluripotency of these cells in vivo, eight to ten transgenic ES cells were injected into 8–16 cell bovine embryos. A total of 99 chimeric embryos were produced, 22 (22%) of them reached blastocyst stage and 10 of those were transferred into five recipient cows. Six calves were born (60%) and, upon ear sample screening by PCR ampliciation and Southern blot hybridization of the amplified product to a $\beta$-galactosidase fragment, one calf was detected positive (17%). In situ DNA hybridization indicated that about 30% of the cells in the spleen were derived from the ES cells in this calf. Also, the ES cells contributed to cells within the testes.

This work demonstrates that bovine somatic cells can be dedifferentiated and ES cells produced, allowing these cells to be used, not only for the generation of transgenic cattle but, also, in differentiation studies and cell therapy.

Example 5

Expression of Exogenous DNA by Cloned Transgenic Cattle

Fibroblasts from female Holstein fetuses are established in culture using the methods described above. Cells are plated at a concentration of 2–3×10$^6$ cells/ml in 100 mm well plates and cultured with alpha-MEM medium (BioWhittaker, Walkersville, Md.) supplemented with 10% FCS, 100 IU/ml penicillin and 50 $\mu$l/ml streptomycin. The plates are incubated at 37° C. with 5% $CO_2$. The media is changed every 3 days, and cells passaged regularly upon reaching confluency.

Culture plates sufficient to provide approximately 100,000 propagating fibroblast cells are incubated with trypsin-EDTA solution (0.05% trypsin/0.02% EDTA; GIBCQ, Grand Island, N.Y.) until the cells are in a single cell suspension. The cells are spun-down at 500 xg and resuspended to a concentration of 10$^6$–10$^7$ cells/ml in PBS with potassium concentrations greater than 400 $\mu$g/ml.

The reporter gene is a human serum albumin-neomycin (hSA-neo) linearized gene construct.

Approximately 50 to 100 $\mu$g of the DNA construct is added to the isolated fibroblast cell suspension. The cells and DNA are placed in an electroporation chamber and pulsed with 300–500 V. After the electroporation pulse, the fibroblast cells are transferred back into the growth medium (alpha-MEM medium (BioWhittaker, Walkersville, Md.) supplemented with 10% fetal calf serum (FCS) (Hyclone, Logen, Utah), 100 IU/ml penicillin and 50 $\mu$l/ml streptomycin).

Selection for stable integration of the construct into the fibroblast cells is done over the next 5 to 1L5 days using G418 (400 $\mu$g/ml) as described above. The presence of the construct is confirmed by Southern blot analysis in surviving cell colonies. The cell lines may also be karyo-typed to check for aneuploidy and polyploidy. Surviving transgenic fibroblast colonies are clonally propagated in the presence of greater than 5% serum and are actively propagating.

Cell lines with the construct stably integrated are used for nuclear transfer procedures. General nuclear transfer procedures are described above.

Female cattle are induced to superovulate with an injection of GNRH. Approximately 20 to 24 hours after GNRH injection the in vivo matured oocytes are collected from the ovaries and oviducts of the donor females. The expanded cumulus cells are stripped from the oocytes and the MII chromosomes removed from the oocytes via micromanipulation.

Three to five clonal transgenic fibroblast cell lines are used in the nuclear transfer procedure. Clonal transgenic fibroblasts are incubated with a trypsin/EDTA solution, spun-down, and resuspended in fusion medium. Individual transgenic fibroblasts are placed in the perivitelline space of the recipient enucleated oocyte.

Individual transgenic fibroblast cells are fused with an enucleated oocyte in fusion media using electrofusion to produce a fused NT unit. One fusion pulse consisting of 120V for 15 $\mu$sec in a 500 $\mu$m gap chamber filled with fusion medium is applied to the chamber. This occurs at 24 hours past maturation (hpm). The fused NT units are placed in TL-HEPES medium for 15–30 minutes to allow the fusion to proceed.

The fused NT units are placed in $B_2$ culture media a balanced salt solution that does not contain calcium lactate. The $B_2$ medium contains a protein kinase inhibitor to initiate oocyte activation, thus preventing the fused NT units from forming chromosomes. An hour after initiation of activation, the NT units are exposed to 5 $\mu$M ionomycin for 4 minutes. The fused NT units are washed and resuspended in $B_2$ medium plus a protein kinase inhibitor (6-dimethylamino purine) for three hours. After incubation with the protein kinase inhibitor, the fused NT units are placed into $B_2$ medium without a protein kinase inhibitor and co-cultured with mouse fibroblasts cells or buffalo rat liver (BRL) cells.

The fused NT units are cultured to the blastocyst stage and nonsurgically transferred into a synchronized recipient female animal with 1–2 embryos per recipient. Pregnancies are monitored by ultrasound at 40, 60, and 90 days gestation. Confirmed transgenic offspring are maintained under specified good agricultural practices and herd health programs. The level of expression of hSA in their milk is confirmed over a 30-day period (approximately 2 months after induced lactation).

What is claimed is:

1. An improved method of cloning a non-human mammal by nuclear transfer comprising the introduction of a non-human mammalian donor cell or a non-human mammalian donor cell nucleus into a non-human mammalian enucleated oocyte of the same species as the donor cell or donor cell nucleus to form a nuclear transfer (NT) unit, implantation of the NT unit into the uterus of a surrogate mother of said species, and permitting the NT unit to develop into the cloned mammal, wherein the improvement comprises using as the donor cell or donor cell nucleus a non-quiescent somatic cell or a nucleus isolated from said non-quiescent somatic cell.

2. The method of claim 1, wherein the fetus develops into an offspring.

3. The method of claim 1, wherein the donor cell or donor cell nucleus is from mesoderm.

4. The method of claim 1, wherein the donor cell or donor cell nucleus is from endoderm.

5. The method of claim 1, wherein the donor cell or donor cell nucleus is from ectoderm.

6. The method of claim 1, wherein the donor cell or donor cell nucleus is from a fibroblast.

7. The method of claim 1, wherein the donor cell or donor cell nucleus is from an ungulate.

8. The method of claim 1, wherein the donor cell or donor cell nucleus is from an ungulate selected from the group consisting of bovine, ovine, porcine, equine, caprine and buffalo.

9. The method of claim 1, wherein the donor cell or donor cell nucleus is from a non-human mammalian fetus.

10. The method of claim 1, wherein the donor cell or donor cell nucleus is from an adult non-human mammalian cell.

11. The method of claim 1, wherein the donor cell or donor cell nucleus is selected from the group consisting of epithelial cells, neural cells, epidermal cells, keratinocytes, hematopoietic cells, melanocytes, chondrocytes, B-lymphocytes, T-lymphocytes, erythrocytes, macrophages, monocytes, fibroblasts, muscle cells, and nuclei isolated therefrom.

12. The method of claim 1, wherein the donor cell or donor cell nucleus is from an organ selected from the group consisting of skin, lung, pancreas, liver, stomach, intestine, heart, reproductive organ, bladder, kidney, and urethra.

13. The method of claim 1, wherein the oocyte is matured in vitro or in vivo prior to enucleation.

14. The method of claim 1, wherein the oocyte is matured in vitro prior to enucleation.

15. The method of claim 1, wherein the oocyte is enucleated by microsurgical methods.

16. The method of claim 1, wherein the oocyte is enucleated about 10 to 40 hours after initiation of in vitro maturation.

17. The method of claim 1, wherein the oocyte is matured in vivo prior to enucleation.

18. The method of claim 1, wherein the non-human mammal is bovine.

19. An improved method of cloning a non-human mammal by nuclear transfer comprising the introduction of a non-human mammalian donor cell or a non-human mammalian donor cell nucleus into a non-human mammalian enucleated oocyte of the same species as the donor cell or donor cell nucleus to form a nuclear transfer (NT) unit, implantation of the NT unit into the uterus of a surrogate mother of said species, and permitting the NT unit to develop into the cloned mammal, wherein the improvement comprises using as the donor cell or donor cell nucleus a non-quiescent somatic cell or a nucleus isolated from said non-quiescent somatic cell, and wherein the donor cell or donor cell nucleus has been genetically transformed to comprise at least one addition, substitution or deletion of a nucleic acid sequence.

20. A method of cloning a non-human mammal by nuclear transfer comprising the following steps:

(i) inserting a desired non-human mammalian non-quiescent somatic cell or a nucleus isolated from said non-quiescent somatic cell, into a non-human mammalian enucleated oocyte of the same species under conditions suitable for the formation of the nuclear transfer (NT) unit;

(ii) activating the resultant nuclear transfer unit;

(iii) culturing said activated NT unit until greater than the 2-cell developmental stage; and (iv) transferring said cultured NT unit to a host non-human mammal of the same species such that the NT unit develops into a non-human mammal.

21. An improved method of cloning a non-human mammalian fetus by nuclear transfer comprising the introduction of a non-human mammalian donor cell or a non-human mammalian donor cell nucleus into a non-human mammalian enucleated oocyte of the same species as the donor cell or donor cell nucleus to form a nuclear transfer (NT) unit, implantation of the NT unit into the uterus of a surrogate mother of the same species, and permitting the NT unit to develop into the mammalian fetus, wherein the improvement comprises using as the donor cell or donor cell nucleus a non-quiescent somatic cell or a nucleus isolated from said somatic cell.

22. An improved method of cloning a non-human mammalian fetus by nuclear transfer comprising the introduction of a non-human mammalian donor cell or a non-human mammalian donor cell nucleus into a non-human mammalian enucleated oocyte of the same species as the donor cell or donor cell nucleus to form a nuclear transfer (NT) unit, implantation of the NT unit into the uterus of a surrogate mother of the same species, and permitting the NT unit to develop into the mammalian fetus, wherein the improvement comprises using as the donor cell or donor cell nucleus a non-quiescent somatic cell, or a nucleus isolated from said proliferating somatic cell, and wherein the donor cell or donor cell nucleus has been genetically modified to comprise at least one addition, substitution or deletion of a nucleic acid sequence.

23. A method of cloning a non-human mammalian fetus by nuclear transfer comprising the following steps:
   (i) inserting a desired non-human mammalian non-quiescent somatic cell, or a nucleus isolated from said non-quiescent somatic cell, into a non-human mammalian enucleated oocyte of the same species under conditions suitable for the formation of a nuclear transfer (NT) unit;
   (ii) activating the resultant nuclear transfer unit;
   (iii) culturing said activated NT unit until greater than the 2-cell developmental stage; and
   (iv) transferring said cultured NT unit to a host non-human mammal of the same species such that the NT develops into a fetus.

* * * * *